Figure 4:
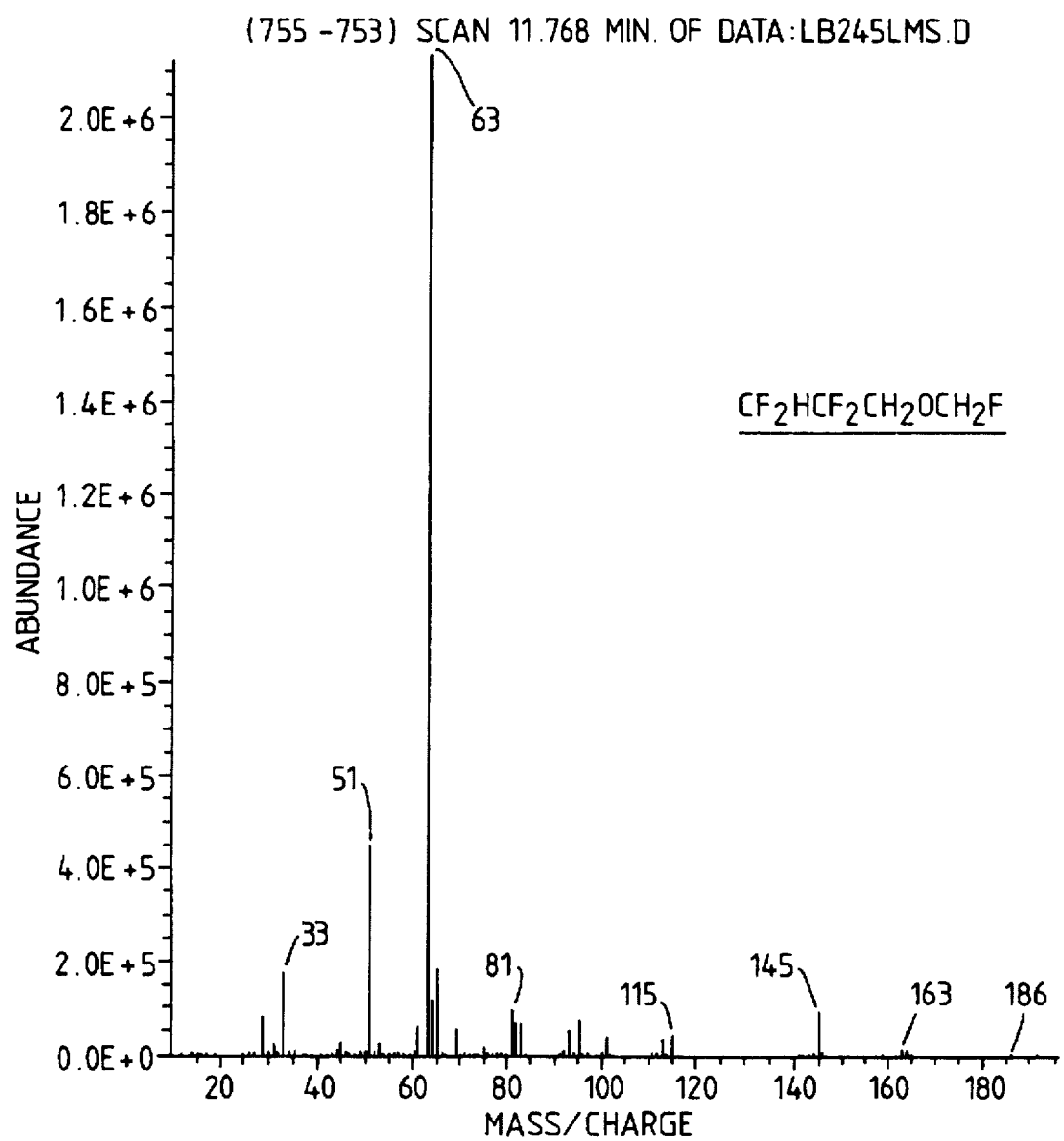

United States Patent [19]

Burgess et al.

[11] Patent Number: 5,750,807
[45] Date of Patent: May 12, 1998

[54] PRODUCTION OF HYROFLUOROCARBONS

[75] Inventors: Leslie Burgess; Jane Lesley Butcher, both of Runcorn; Thomas Anthony Ryan, Cheshire; Peter Paul Clayton, Runcorn, all of England

[73] Assignee: Imperial Chemical Industries PLC, London, England

[21] Appl. No.: 446,524

[22] Filed: May 19, 1995

Related U.S. Application Data

[60] Continuation of Ser. No. 93,861, Jul. 20, 1993, abandoned, which is a division of Ser. No. 988,679, Dec. 10, 1992, abandoned.

[30] Foreign Application Priority Data

Dec. 11, 1991 [GB] United Kingdom ............ 9126355

[51] Int. Cl.$^6$ ............................ C07C 21/18; C07C 43/00
[52] U.S. Cl. ............................................ 570/142; 568/683
[58] Field of Search ............................. 568/683; 570/142

[56] References Cited

U.S. PATENT DOCUMENTS 2,992,276  7/1961  Weinmayr .
5,504,263  4/1996  Burgess et al. .

OTHER PUBLICATIONS

Lovelace Aliphatic Fluorine Comp. (1958) p. 47.

Wagner et al Synth Org Chem. (1965) p. 230.

March, Advanced Organic Chemistry, Second Edition (1982), pp. 827–828 and 1180.

Wagner, Synthetic Org. Chem., pp. 92–93 (1953).

Lovelace, Aliphatic Fluorine Comp., p. 47 (1958).

*Primary Examiner*—Alan Siegel
*Attorney, Agent, or Firm*—Pillsbury Madison & Sutro LLP

[57] ABSTRACT

A process for the production of a hydro(halo)fluorocarbon which comprises heating an α-fluoroether in the vapor phase at elevated temperature. α-fluoroethers are obtained by reacting a non-enolisable aldehyde with hydrogen fluoride to form an intermediate and reacting the intermediate with an alcohol or a halogenating agent. Novel α-fluoroethers are also provided.

6 Claims, 5 Drawing Sheets

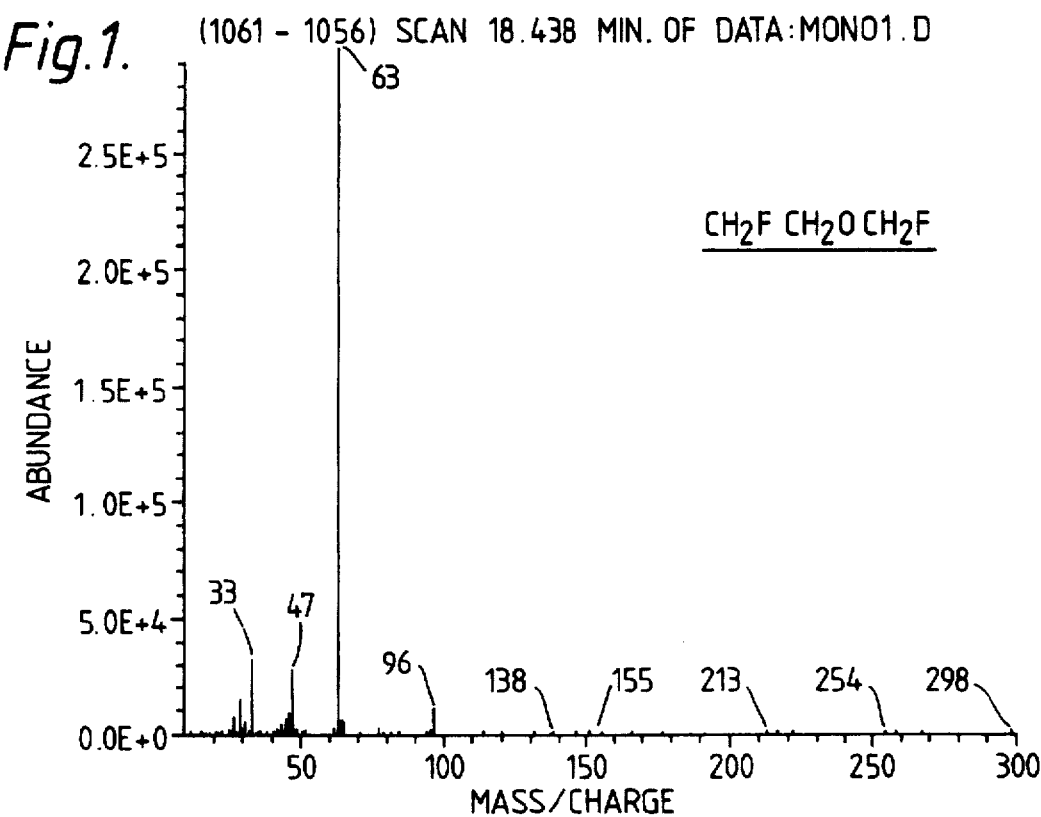
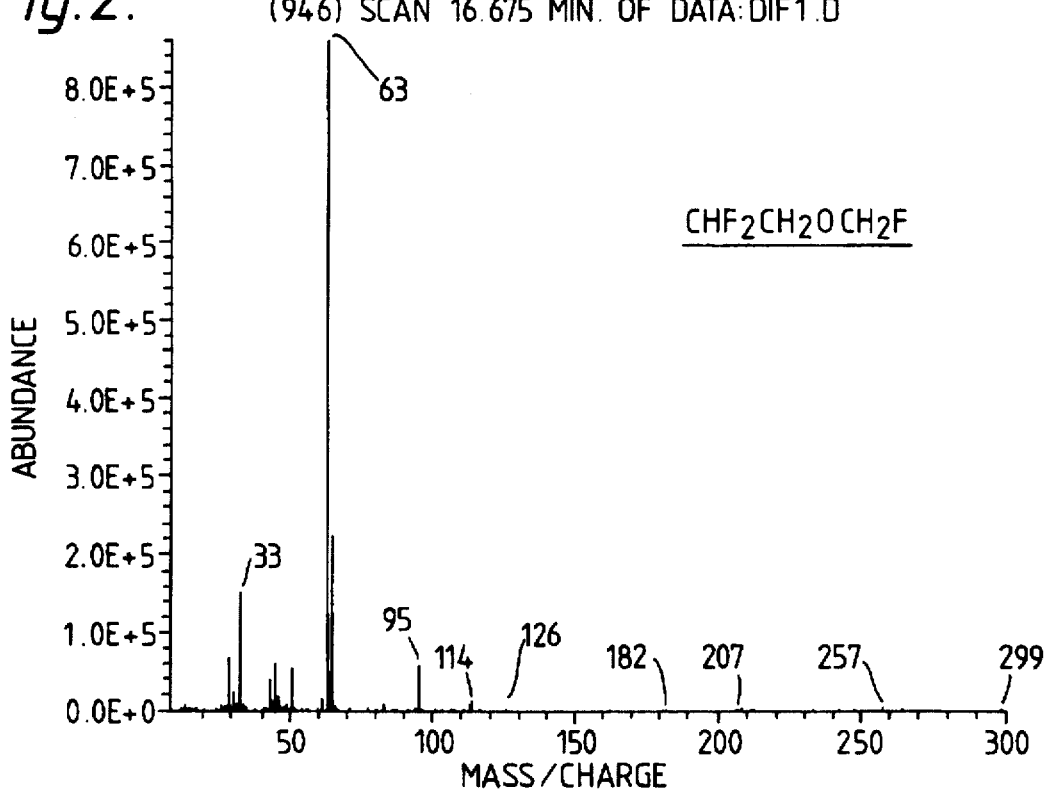

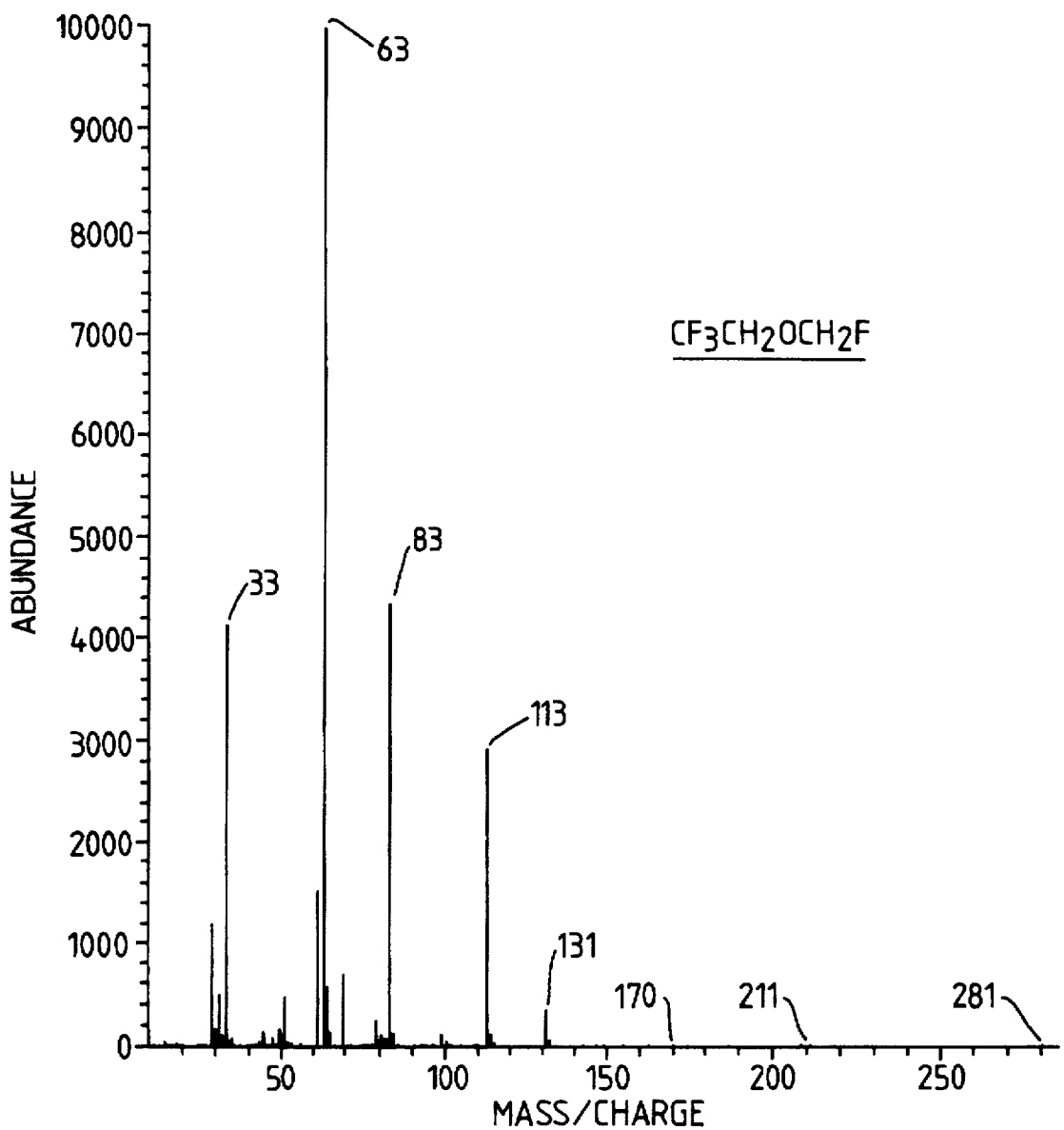

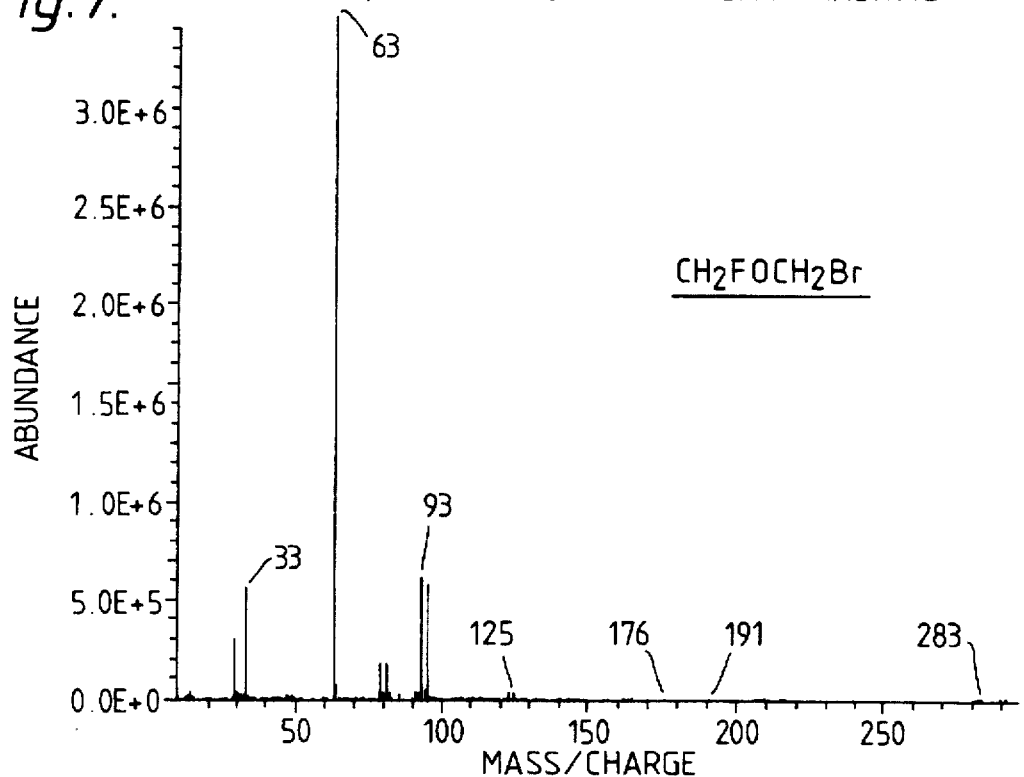
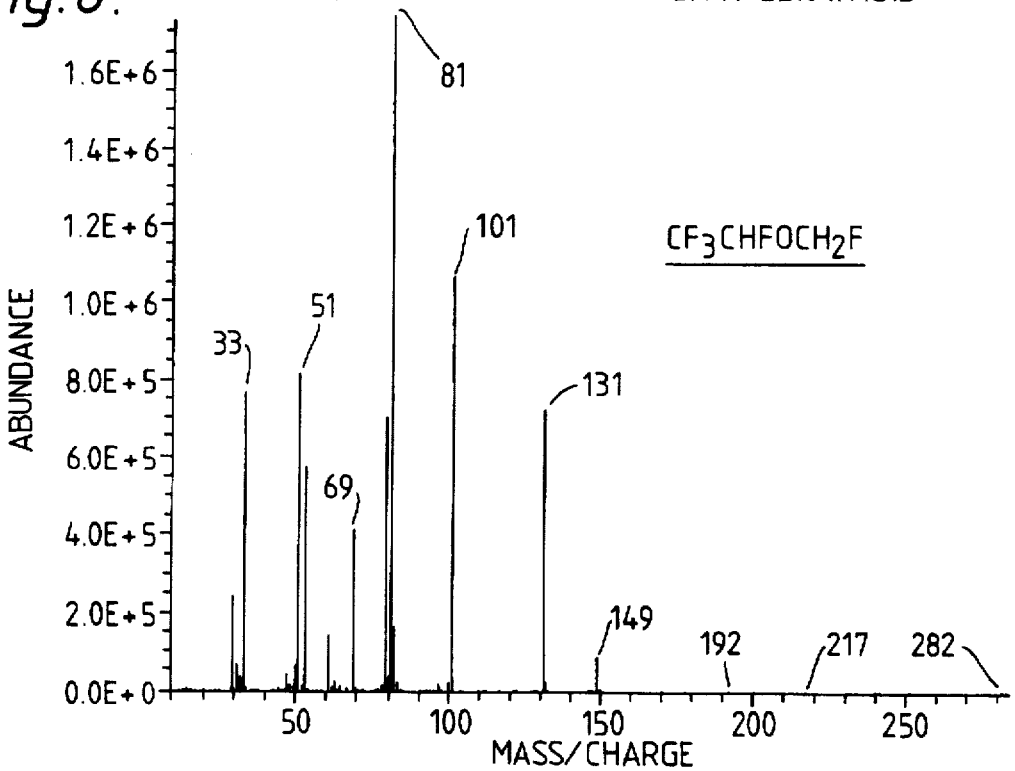

PRODUCTION OF HYROFLUOROCARBONS

This is a continuation of application Ser. No. 08/093,861, filed on Jul. 20, 1993 now abandoned, which is a division of Ser. No. 07/988,679, filed Dec. 10, 1992 now abandoned.

This invention relates to a process for the production of hydrofluorocarbons from α-fluoroethers and a process for the production of α-fluoroethers and novel α-fluoroethers suitable for use in the production of hydrofluorocarbons, particularly to a process for the production of hydrofluoroalkanes.

In recent years chlorofluorocarbons, which are used on a large scale around the world, have been perceived as having an adverse effect on the ozone layer and/or as contributing to global warming. Chlorofluorocarbons are used, for example, as refrigerants, as foam blowing agents, as cleaning solvents and as propellants for aerosol sprays in which the variety of applications is virtually unlimited. Consequently, much effort is being devoted to finding suitable replacements for chlorofluorocarbons which will perform satisfactorily in the many applications in which chlorofluorocarbons are used but which will not have the aforementioned environmentally harmful effects. One approach in the search for suitable replacements has centred on fluorocarbons which do not contain chlorine but which may contain hydrogen, that is hydrofluorocarbons, of which many have been proposed as suitable replacements.

Several methods for the preparation of hydrofluorocarbons are known but many of these methods involve the use of chlorine-containing starting materials and the production of chlorine-containing by-products.

The present invention provides a chlorine-free process for the production of hydrofluorocarbons and a process for the production of hydrohalofluorocarbons.

According to the present invention there is provided a process for the production of a hydro(halo)fluorocarbon which comprises heating an α-fluoroether in the vapour phase at an elevated temperature.

By an α-fluoroether there is meant an ether having a fluorine atom attached to a carbon atom in the α-position relative to the oxygen atom, that is an ether containing the group —C—O—CF— and thus an ether having the general formula R—O—CFR$^1$R$^2$, wherein R, R$^1$ and R$^2$ are as hereinafter defined.

We have found that α-fluoroethers of formula R—O—CF—R$^1$R$^2$ may be caused to breakdown upon heating to yield a hydro(halo)fluorocarbon R—F and a compound containing a carbonyl group, usually an aldehyde R$^1$R$^2$CO. The ether apparently breaks down by transference of an α-fluorine atom from one α-carbon atom to the other α-carbon atom to yield a hydro(halo)fluorocarbon R—F (referred to hereafter as the fluorine-exchange product). The ether may in some cases also break down by transference of an α-hydrogen atom so that a hydro(halo)fluorocarbon R—H (referred to hereafter as the hydrogen-exchange product) may also be produced. α-fluoro-ethers may therefore be utilised as useful starting materials for the production of hydro(halo)fluoroalkanes.

In the α-fluoroether R—O—CF—R$^1$R$^2$, the group R may generally take any form provided that it comprises at least one carbon atom, and the group R may for example be saturated or unsaturated, cyclic or acyclic. Furthermore, the group R may be aliphatic or aromatic and it may be a substituted group such as a halo-substituted group.

The process of the invention is useful in particular for the production of hydrofluoroalkanes from ethers in which the R group is an alkyl group which may comprise one, two or even more carbon atoms, say up to 6 or even more carbon atoms. The alkyl group R will usually be a straight chain alkyl group although it may also be a branched chain alkyl group. The group R may comprise only carbon and hydrogen although it may contain other atoms such as halogen atoms; usually the group R will be a fluorinated group.

The α-fluoroether will typically be an α-fluoroalkyl ether, that is an ether of formula R—O—CF—R$^1$R$^2$ wherein R$^1$ and R$^2$ each represents a hydrogen atom or an alkyl or substituted alkyl group which may comprise one, two or even more carbon atoms, say up to 6 or even more carbon atoms, provided that where R$^1$ and R$^2$ both are hydrogen, R is not the —CH$_2$F group. The alkyl groups R$^1$ and R$^2$ will usually be straight chain alkyl groups although they may also be branched chain alkyl groups. The groups R$^1$ and R$^2$ may comprise only carbon and hydrogen although they may be substituted alkyl groups; usually the groups R$^1$ and R$^2$ will be fluorinated groups. Typically at least one of R$^1$ and R$^2$ will be a hydrogen atom.

According to a preferred embodiment of the invention there is provided a process for the production of hydro(halo)fluoroalkanes which comprises heating an α-fluoroether having the formula R—O—CF—R$^1$R$^2$ wherein R is an alkyl or substituted alkyl group comprising from 1 to 6 carbon atoms and R$^1$ and R$^2$ each is H or an alkyl group containing from 1 to 6 carbon atoms.

The α-fluoroether is preferably an α-fluoromethylether, R—O—CFH$_2$, or a tetrafluoroethylether R—O—CFH—CF$_3$, since these α-fluoroethers are readily prepared and on heating in the vapour phase to elevated temperature yield particularly useful hydrofluorocarbons.

The α-fluoromethylether may be, for example, FCH$_2$—O—CH$_3$ (fluoromethyl-methylether), FCH$_2$—O—CH$_2$CF$_2$H (1,1,-difluoroethyl-fluoromethyl ether), or FCH$_2$—O—CH$_2$CF$_3$ (1,1,1-trifluoroethyl-fluoromethylether), which when heated in the vapour phase to elevated temperature may give the following hydrofluoroalkanes respectively, CH$_3$F, CHF$_2$CH$_2$F and CF$_3$CH$_2$F. The tetrafluoroethylether may be, for example, CF$_3$CHF—O—CH$_2$CF$_3$ or CF$_3$CFH—O—CH$_3$ (which upon heating in the vapour phase to elevated temperature may yield 1,1,1,2-tetrafluoroethane) or CF$_3$CFH—O—CFHCF$_3$ or CF$_3$CHF—O—CH$_2$F (which upon heating in the vapour phase to elevated temperature may yield CF$_3$CF$_2$H and/or CF$_3$CFH$_2$).

According to an embodiment of the invention there is provided a process for the production of 1,1,1,2-tetrafluoroethane comprising heating an α-fluoroalkylether selected from the group consisting of FCH$_2$—O—CH$_2$CF$_3$, FCH$_2$—O—CHFCF$_3$, CF$_3$CHF—O—CH$_2$CF$_3$ and CF$_3$CFH—O—CH$_3$ in the vapour phase at an elevated temperature.

According to another embodiment of the invention there is provided a process for the production of pentafluoroethane comprising heating CF$_3$CFH—O—CFHCF$_3$ or CF$_3$CFH—O—CH$_2$F in the vapour phase at an elevated temperature.

Heating of the α-fluoroether may advantageously be carried out in the presence of hydrogen fluoride vapour since we have found that the presence of hydrogen fluoride may, at least with certain α-fluoroethers, tend to increase the yield of hydro(halo)fluorocarbon obtained.

Heating of the α-fluoroether may also advantageously be performed in the presence of a catalyst. The conversion of the α-fluoroether and selectivity to the hydro(halo)fluoroalkane are dependent in particular upon the catalyst in the presence of which the α-fluoroether is heated; we have found that certain catalysts promote a high degree of selectivity to the fluorine-exchange product whilst other catalysts promote a high degree of selectivity to the hydrogen exchange product and still other catalysts yield mixtures of both the fluorine-exchange and hydrogen-exchange products. Furthermore, whether the fluorine-exchange product or hydrogen exchange product is promoted by a particular catalyst is also dependent at least to some extent upon the particular α-fluoroether. Thus with certain α-fluoroethers a particular catalyst may promote fluorine-exchange whilst the same catalyst may promote hydrogen-exchange with other α-fluoroethers.

It is to be understood that the process of the invention may lead to a product comprising a mixture of hydro(halo) fluoroalkanes from a single α-fluoroether. Thus, for example, where the α-fluoroether is $CH_2F$—O—$CH_2CF_3$ the product may be a mixture of $CH_3CF_3$ and $CF_3CH_2F$. Furthermore, desirable mixtures of hydrofluoroalkanes may be produced, as desired, by employing mixtures of α-fluoroethers. Thus, for example, where a mixture of $CH_2F$—O—$CH_2F$ and $CF_3CH_2$—O—$CH_2F$ is heated to elevated temperature, the product may comprise a mixture of $CH_2F_2$, $CH_3F$ and $CF_3CH_2F$.

The catalyst may be for example, a metal, for example a metal selected from the group consisting of nickel, iron, copper and chromium, or an alloy, oxide, fluoride or oxyfluoride thereof, for example chromia or alumina, aluminium or chromium fluoride, or a metal oxyfluoride.

We have found that in general the fluorine-exchange product may be produced with very high selectivity where the catalyst employed is a metal selected from the group consisting of nickel, iron, copper or chromium and in particular where the catalyst is an alloy of at least one of these metals. We especially prefer to employ an alloy of all these metals, for example Hastelloy or stainless steel.

Furthermore we prefer that the alloys are air treated prior to use, that is the alloys are heated to elevated temperature in the presence of air, for example a temperature in the range from 300° C. to 500° C. Alternatively or additionally, the catalyst pre-treatment may comprise heating the catalyst in the presence of hydrogen fluoride.

A further preferred catalyst is chromia which although it may not promote a very high degree of selectivity to the fluorine-exchange product, is a very robust catalyst. Chromia may also be given a pre-treatment prior to its use.

Catalysts which in general lead to the production of the hydrogen-exchange product with a high degree of selectivity include for example catalysts comprising zinc on chromia or zinc impregnated chromia.

The temperature to which the α-fluoroether is heated to produce a hydro(halo)fluoroalkane is such that the α-fluoroether is in the vapour phase and the temperature will therefore depend at least to some extent on the particular α-fluoroether employed. Generally the temperature will be at least 80° C., usually at least 200° C. and preferably at least 350° C. The temperature need be no higher than about 500° C. although higher temperatures, say up to about 700° C., may be used if desired.

The temperature to which the α-fluoroether is heated is also dependant at least to some extent on whether the heating is effected in the presence or absence of a catalyst. Where the heating is effected in the presence of a catalyst the preferred temperature is dependent on the particular catalyst used; generally where one of the aforementioned metals or alloys is present the temperature need not be as high as when one of the aforementioned metals or alloys is not present.

Typically the temperature need be no higher than about 450° C. where a catalyst is used in the presence of hydrogen fluoride. Thus, for example, where the heating is effected in the presence of stainless steel and hydrogen fluoride the temperature is preferably at least about 250° C. and more preferably at least 300° C. but need be no higher than about 400° C., generally no higher than about 350° C. However, where the fluorination catalyst is chromia in the presence of hydrogen fluoride the temperature is preferably from about 180° C. to about 320° C., more preferably from about 200° C. to about 280° C.

The process of the invention is conveniently carried out at about ambient pressure although superatmospheric or subatmospheric pressures may be used if desired. Superatmospheric pressures up to about 10 bar at lower temperatures are generally preferred since the yield of hydro(halo) fluorocarbons is often increased under such conditions.

After completion of the reaction, the hydro(halo) fluorocarbon may be isolated from unchanged starting materials and undesired by-products using conventional procedures, for example distillation.

It is particularly convenient to operate the process of the invention as a continuous process wherein unchanged α-fluoroether and any hydrogen fluoride present in the hydro(halo)fluorocarbon product stream are recycled to the reaction zone.

A particularly convenient and thus preferred general method for the production of the α-fluoroether is by reacting a non-enolisable aldehyde with hydrogen fluoride (in the liquid phase or in the vapour phase) and reacting the resulting intermediate with an alcohol or a halogenating agent to form an α-fluoroether.

A non-enolisable aldehyde is required in order that the aldehyde is not polymerised in hydrogen fluoride when the two are reacted together.

According to a preferred embodiment of the invention there is provided a process for the production of a hydro (halo)fluorocarbon which comprises (a) reacting a non-enolisable aldehyde with hydrogen fluoride to form an intermediate and reacting the intermediate with an alcohol or a halogenating agent to produce an α-fluoroether and (b) treating the α-fluoroether whereby to form a hydro(halo) fluoroalkane. The treatment of the α-fluoroether whereby to form a hydro(halo)fluoroalkane may be, for example, as hereinbefore described by heating to elevated temperature in the vapour phase.

The intermediate obtained by reacting the non-enolisable aldehyde with hydrogen fluoride may be reacted with the alcohol or halogenating agent in a number of ways. The aldehyde and the hydrogen fluoride may be reacted in the presence of alcohol or halogenating agent. Alternatively the aldehyde and the hydrogen fluoride may be reacted to form an equilibrium mixture containing the intermediate and the alcohol or halogenating agent may be added to the equilibrium mixture. In a modification of this alternative, the intermediate may be separated from the equilibrium mixture before it is reacted with the alcohol or halogenating agent.

It is to be understood that the intermediate derived from the non-enolisable aldehyde and hydrogen fluoride may itself be an α-fluoroether and that incomplete reaction of such an intermediate with the alcohol or halogenating agent may therefore result in a mixture of α-fluoroethers. Whilst an intermediate α-fluoroether is not the starting material for use in the process for producing a hydro(halo) fluorocarbon according to the invention, a mixture of α-fluoroethers containing unreacted intermediate α-fluoroether is a suitable starting material for use in the invention.

α-fluoroethers containing halogen other than fluorine, particularly chlorine or bromine, may be employed as starting materials for the production of hydrohalofluorocarbons containing a halogen atom other than fluorine. Such α-fluoroethers may be produced by reacting the intermediate derived from a non-enolisable aldehyde and hydrogen fluoride with a suitable halogenating agent to effect exchange of fluorine by halogen other than fluorine. The halogenating agent may be a halogen-containing Lewis acid such as antimony pentachloride, niobium pentachloride, aluminium chloride and sodium bromide.

The non-enolisable aldehyde is preferably formaldehyde or trifluoroacetaldehyde; formaldehyde is particularly preferred. In an embodiment of the invention both formaldehyde and trifluoroacetaldehyde are reacted with hydrogen fluoride to produce a mixture of $CF_3CFH$—O—$CH_2F$ and $CH_2F$—O—$CH_2F$. The mixture of aldehydes generates an alcohol in situ and the resulting α-fluoroether mixture may be converted to hydrofluoroalkanes. If desired, a separate alcohol may be added to the mixture to produce further α-fluoroethers.

In the embodiment of the invention, comprising the steps of (a) producing an α-fluoroether and (b) heating the α-fluoroether in the vapour phase at an elevated temperature to form a hydro(halo)fluorocarbon, both of steps (a) and (b) employ elevated temperature and both may employ a catalyst so that in practice at least a part of the α-fluoroether produced in step (a) may be converted to a hydro(halo) fluorocarbon (step b) without a change in reaction conditions. However, we have found that for optimum results different catalysts are preferred in step (a) and step (b); the process then comprises operation of step (a) using a first catalyst to produce an α-fluoroether and a hydro(halo) fluorocarbon and operation of step (b) using a second catalyst to convert unreacted α-fluoroether from step (a) to the hydro(halo)fluorocarbon.

The non-enolisable aldehyde may be provided in any of its known forms. Thus formaldehyde may be provided, for example, in one of its polymeric forms, paraformaldehyde or trioxane, or in its monomeric form which may be provided, for example, from a process stream in which it has been freshly made, for example by the oxidation of methanol. Trifluoroacetaldehyde may be provided, for example, in its hydrated form $CF_3CH(OH)_2$ or in its deydrated form $CF_3CHO$.

Accordingly, whenever used herein the term non-enolisable aldehyde is to be understood as including non-enolisable aldehydes in any of their known forms.

In general, where formaldehyde is used as the non-enolisable aldehyde, a polymeric form of formaldehyde such as paraformaldehyde is preferred where the formaldehyde is dissolved in liquid hydrogen fluoride. Paraformaldehyde and trioxane dissolve readily in liquid hydrogen fluoride and the production of the intermediate for the α-fluoroether may be conveniently carried out by dissolving paraformaldehyde or trioxane in liquid hydrogen fluoride at about room temperature and at about atmospheric pressure.

The molar ratio of the non-enolisable aldehyde to hydrogen fluoride may vary considerably, for example in the range about 1:0.5 to 1:50 but in general a stoichiometric excess of hydrogen fluoride is preferred. Typically, the molar ratio of non-enolisable aldehyde to hydrogen fluoride will be in the range about 1:2 to about 1:10.

In one embodiment of the invention the non-enolisable aldehyde is reacted with hydrogen fluoride in the presence of an alcohol. In this case, the alcohol may be generated in situ. Thus, for example, reaction of the non-enolisable aldehyde trifluoroacetaldehyde with hydrogen fluoride is believed to yield an alcohol $CF_3CHFOH$ which may then condense to give the α-fluoroether $CF_3CFH$—O—$CFHCF_3$.

A wide range of α-fluoroethers may be produced by adding a separate alcohol. Where a separate alcohol is added, it may be added at the same time as the hydrogen fluoride and non-enolisable aldehyde, or it may be added subsequently to the mixture of aldehyde and hydrogen fluoride. Furthermore the alcohol may be first added to the hydrogen fluoride and the aldehyde may then be added to this reaction mixture. Thus the order of addition of the hydrogen fluoride, aldehyde and alcohol is not critical.

Where the alcohol is added separately, a primary alcohol is preferred which may have the general formula R—OH where R is as hereinbefore described. The alcohol must be inert to hydrogen fluoride and the α-fluoroether. The group R becomes the R group of the ether produced having the general formula R—O—CF—$R^1R^2$, the groups $R^1$ and $R^2$ being as hereinbefore described.

The group R will usually be a straight chain alkyl or substituted alkyl group although it may also be a branched chain group. The R group may comprise only hydrogen and carbon, for example the R group may be $CH_3$ or $C_2H_5$. Preferably however, the R group will be fluorinated, for example the R group may be $FCH_2CH_2$—, $HCF_2CH_2$—, $CF_3CH_2$—, $(CF_3)_2CH$—, or $CF_2HCF_2CH_2$—. The alcohol R—OH is preferably a primary alcohol and may be, for example, methanol, ethanol, 2-monofluoroethanol, 2,2-difluoroethanol, 2,2,2-trifluoroethanol, hexafluoroisopropanol or 1,1,2,2-tetrafluoropropanol. Some at least of the alcohols may be generated in situ, for example by adding an epoxide to the non-enolisable aldehyde/hydrogen fluoride mixture. Thus for example, 2-monofluoroethanol may be generated in situ by the addition of ethylene glycol which reacts with hydrogen fluoride to produce 2-monofluoroethanol.

Where the alcohol is added separately, it may be added in similar proportions as the non-enolisable aldehyde, that is in the molar ratio of alcohol to hydrogen fluoride in the range about 1:0.5 to 1:50 but in general a stoichiometric excess of hydrogen fluoride is preferred. The optimum proportion of alcohol added may depend upon the particular alcohol used since we have found that with certain alcohols, the addition of too great a proportion of the alcohol leads to the formation of an undesirable acetal rather than the required α-fluoroether. Typically the molar ratio of alcohol to hydrogen fluoride will be in the range of from about 1:2 to about 1:10.

A number of the α-fluoroethers produced by the process of the invention are novel compounds and the following α-fluoroethers are provided according to the invention:

Fluoromethyl-fluoroethyl ether of formula $CH_2FCH_2OCH_2F$ whose mass spectrum is shown in FIG. 1 of the drawings.

Fluoromethyl-difluoroethyl ether of formula $CHF_2CH_2OCH_2F$ whose mass spectrum is shown in FIG. 2 of the drawings.

Fluoromethyl-trifluoroethyl ether of formula $CF_3CH_2OCH_2F$ whose mass spectrum is shown in FIG. 3 of the drawings.

Fluoromethyl-tetrafluoropropyl ether of formula $CHF_2F_2CH_2OCH_2F$ whose mass spectrum is shown in FIG. 4 of the drawings.

Figure 5:
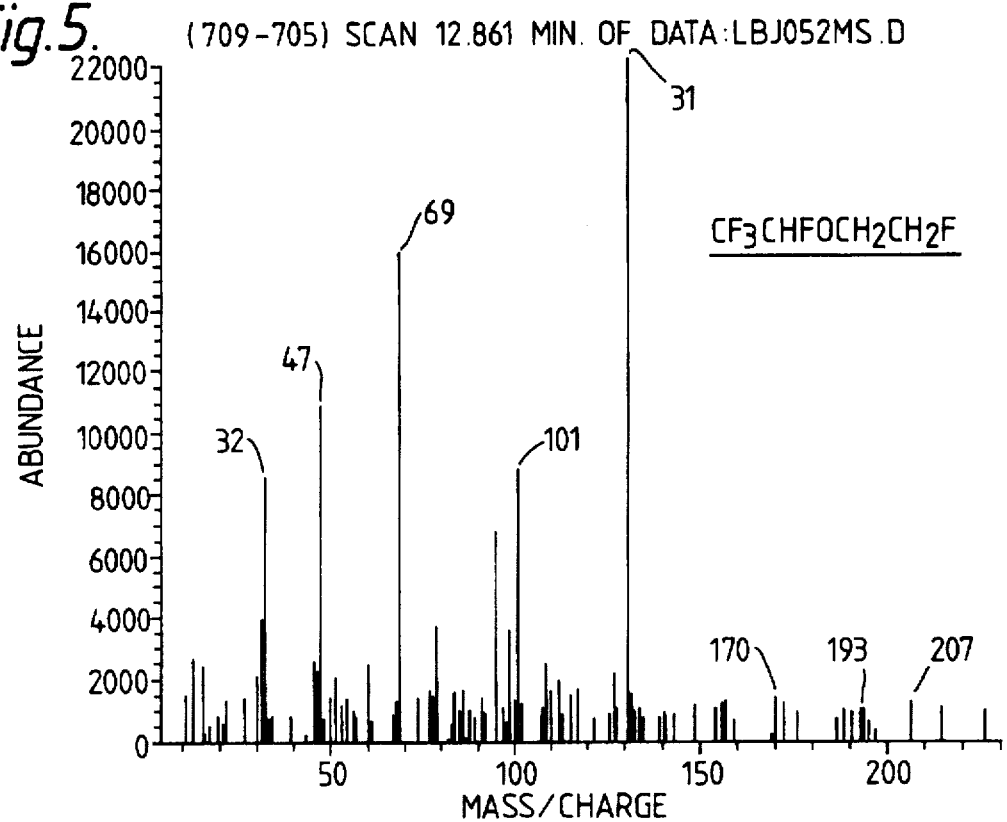

Fluoroethyl-tetrafluoroethyl ether of formula $CF_3CHFOCH_2CH_2F$ whose mass spectrum is shown in FIG. 5 of the drawings.

Figure 6:
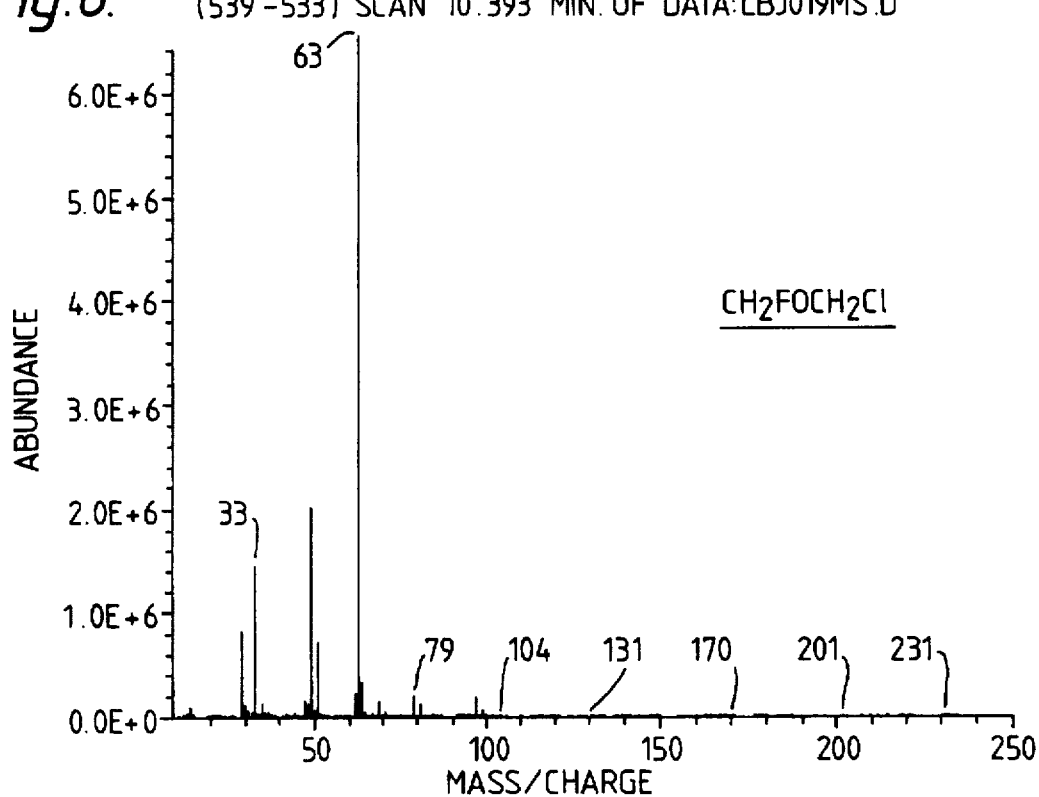

Fluoromethyl-chloromethyl ether of formula $CH_2FOCH_2Cl$ whose mass spectrum is shown in FIG. 6 of the drawings.

Fluoromethyl-bromomethyl ether of formula $CH_2FOCH_2Br$ whose mass spectrum is shown in FIG. 7 of the drawings.

FIG. 8 of the drawings shows the mass spectrum of fluoromethyl-tetrafluoroethyl ether of formula $CF_3CHFOCH_2F$. This ether has been isolated from the mixture in which it was produced and its boiling point was determined as 47.5° C.

The α-fluoroether may be isolated from the mixture in which it is produced, and any by-products, before the α-fluoroether is heated to elevated temperature. The ether may be isolated, for example, by adding alkali to the mixture and heating the resulting alkaline solution, for example up to about 50° C., in order to drive off the α-fluoroether. Alternatively the α-fluoroether may conveniently be isolated by contacting the product stream with water at a temperature in the range from about 50° C. to about 80° C. The α-fluoroether may then be collected in a cold trap or passed directly to the heating zone.

The α-fluoroether may be introduced into the heating zone in undiluted form although it is generally convenient to introduce it in conjunction with a diluent such as an inert carrier gas, for example nitrogen.

In the embodiment of the invention wherein the α-fluoroether is generated by dissolving a non-enolisable aldehyde in liquid hydrogen fluoride and reacting the resulting intermediate with an alcohol, the α-fluoroether and the hydrogen fluoride in which it is dissolved may be vaporised together into the heating zone together with any unreacted aldehyde in the solution. In this case it may be a mixture of α-fluoroethers which is vaporised into the heating zone, so that a mixture of hydrofluoroalkanes are produced by heating the mixture of α-fluoroethers to elevated temperature. We especially prefer that the α-fluoroether and optionally hydrogen fluoride are separated from water which is also produced by the reaction of the non-enolisable aldehyde with hydrogen fluoride. Thus the α-fluoroether and optionally hydrogen fluoride are preferably passed to the heating zone in the substantial absence of water. Separation of the α-fluoroether and optionally hydrogen fluoride from water may be achieved in any suitable manner, conveniently for example by vaporising the α-fluoroether and optionally hydrogen fluoride from the product mixture or by contacting the product mixture with a solid drying agent. Thus for example a stream of an inert gas, for example nitrogen may be sparged through the product mixture.

Accordingly, in a further embodiment of the invention there is provided a process for the production of a hydrofluoroalkane which comprises the steps of (a) reacting a non-enolisable aldehyde with liquid hydrogen fluoride and reacting the resulting intermediate with an alcohol to produce an α-fluoroether, (b) separating at least some water from the product of step (a) and (c) passing the α-fluoroether and hydrogen fluoride from step (b) in the vapour phase into a reaction zone at elevated temperature.

In the embodiment where the non-enolisable aldehyde, hydrogen fluoride and alcohol are reacted in the vapour phase to produce the α-fluoroether, the product stream may be passed directly to a second reaction zone, after drying if desired, optionally together with additional hydrogen fluoride and a diluent such as nitrogen gas.

Where the α-fluoroether is generated in the liquid phase, the non-enolisable aldehyde/hydrogen fluoride/alcohol liquid mixture is preferably held in the liquid phase in order to prevent any premature decomposition of the α-fluoroether such as may occur in the vapour phase. The temperature of the liquid mixture is therefore conveniently maintained below the boiling point of the product mixture, preferably at a temperature from about −10° C. to about 20° C.

The invention is illustrated, but not limited, by the following examples.

PRODUCTION OF α-FLUOROETHERS

EXAMPLE 1

24 g of anhydrous liquid hydrogen fluoride were added with cooling to 5 g of trioxane and to this mixture was added 0.042 moles of methanol. The mixture was sampled immediately and analysed by Gas chromatography/Mass Spectrometry. The vol % composition of the mixture was determined to be:

| Component | vol % composition |
| --- | --- |
| methanol | 1.61 |
| $CH_3$—O—$CH_2F$ | 14.4 |
| $CH_2F$—O—$CH_2F$ | 66.8 |
| $CH_3$—O—$CH_2$—O—$CH_3$ | 13.7 |
| Trioxane | 3.4 |

EXAMPLE 2

The procedure of example 1 was repeated except that 0.073 moles of ethanol were employed. The volume % composition of the mixture was determined to be:

| Component | vol % composition |
| --- | --- |
| ethanol | 5.7 |
| $CH_3CH_2$—O—$CH_2F$ | 17.8 |
| $CH_2F$—O—$CH_2F$ | 36.5 |
| $CH_3CH_2$—O—$CH_2$—O—$CH_2CH_3$ | 35.2 |
| Trioxane | 2.1 |

EXAMPLE 3

The procedure of example 1 was repeated except that 0.073 moles of 2-fluoroethanol were employed. The volume % composition of the mixture was determined to be:

| Component | vol % composition |
| --- | --- |
| 2-fluoroethanol | 5.7 |
| $CH_2FCH_2$—O—$CH_2F$ | 29.0 |
| $CH_2F$—O—$CH_2F$ | 45.0 |
| $CH_2FCH_2$—O—$CH_2$—O—$CH_2CH_2F$ | 10.0 |
| Trioxane | 4.7 |

EXAMPLE 4

The procedure of example 1 was repeated except that 0.073 moles of 2,2-difluoroethanol were employed. The volume % composition of the mixture was determined to be:

| Component | vol % composition |
| --- | --- |
| 2,2-difluoroethanol | 4.7 |
| $CF_2HCH_2$—O—$CH_2F$ | 59.2 |
| $CH_2F$—O—$CH_2F$ | 30.8 |
| $CF_2HCH_2$—O—$CH_2$—O—$CH_2CF_2H$ | 3.6 |
| Trioxane | 0.0 |

EXAMPLE 5

The procedure of example 1 was repeated except that 0.073 moles of 2,2,2-trifluoroethanol were employed. The volume % composition of the mixture was determined to be:

| Component | vol % composition |
|---|---|
| 2,2,2-trifluoroethanol | 11.1 |
| CF$_3$CH$_2$—O—CH$_2$F | 62.3 |
| CH$_2$F—O—CH$_2$F | 17.0 |
| CF$_3$CH$_2$—O—CH$_2$—O—CH$_2$CF$_3$ | 9.5 |
| Trioxane | 0.0 |

EXAMPLE 6

The procedure of example 1 was repeated except that 0.042 moles of 1,1,2,2-tetrafluoropropanol were employed. The weight % composition of the mixture was determined to be:

| Component | vol % composition |
|---|---|
| 1,1,2,2-tetrafluoropropanol | 7.85 |
| CF$_2$HCF$_2$CH$_2$—O—CH$_2$F | 59.6 |
| CH$_2$F—O—CH$_2$F | 29.3 |
| CF$_2$HCF$_2$CH$_2$—O—CH$_2$—O—CH$_2$CF$_2$CF$_2$H | 1.4 |
| Trioxane | 1.9 |

EXAMPLE 7

0.5 cms$^3$ of trifluoroacetaldehyde in the form of its hydrate CF$_3$CH(OH)$_2$ was added to 6 cms$^3$ of anhydrous liquid hydrogen fluoride and the mixture was analysed by nuclear magnetic resonance. Analysis indicated that the ether CF$_3$CHF—O—CHFCF$_3$ was the major product.

EXAMPLE 8

6 cms$^3$ of anhydrous liquid hydrogen fluoride were added with cooling to 1.25 g of paraformaldehyde and to this mixture was added 0.5 cms$^3$ of CF$_3$CH(OH)$_2$. Gas chromatography and Mass spectrometry indicated that the ethers CF$_3$CHF—O—CH$_2$F and CH$_2$F—O—CH$_2$F were the main products.

DECOMPOSITION OF ETHERS

EXAMPLE 9

The product mixture of example 1 was sparged with nitrogen at a flow rate of 50 cms$^3$ per minute and the sparged mixture was fed to an Inconel tube packed with 200 cms$^3$ of Hastelloy C mesh and heated to an elevated temperature. The off gas was scrubbed with water and analysed by Gas chromatography. At 257° C. the composition of the off gas was:

| Component. | % v/v. |
|---|---|
| CH$_3$F | 19.2 |
| CH$_2$F$_2$ | 60.8 |
| CH$_2$F—O—CH$_2$F | 20.0 |

EXAMPLE 10

The procedure of example 9 was repeated except that the product mixture of example 5 was sparged with nitrogen and the Inconel tube was packed with 200 cms$^3$ of chromia pellets. At 350° C. the composition of the off gas was:

| Component. | % v/v |
|---|---|
| CH$_3$F | 31.5 |
| CH$_2$F$_2$ | 46.6 |
| CF$_3$CH$_2$F | 13.9 |
| CF$_3$CH$_3$ | 0.4 |
| CH$_2$F—O—CH$_2$F | 1.0 |
| Others | 6.6 |

EXAMPLE 11

The procedure of example 9 was repeated except that the product mixture of example 6 was sparged with nitrogen. Mass spectrometry indicated that 1,1,2,2,3-pentafluoropropane was the major product.

EXAMPLE 12

The procedure of example 9 was repeated except that the product mixture of example 4 was sparged with nitrogen and the Inconel tube was packed with 115 ml (70 g) stainless steel rings which had been air-treated by heating the rings to 350° C. in a stream of air for 4 hours. At 350° C., the composition of the off gas was:

| Component. | % v/v |
|---|---|
| CH$_2$F$_2$ | 4.5 |
| CF$_2$HCH$_2$F | 23.8 |
| CF$_2$HCH$_2$OH | 4.2 |
| CH$_2$F—O—CH$_2$F | 44.5 |
| CF$_2$HCH$_2$—O—CH$_2$F | 21.1 |
| Others | 1.9 |

EXAMPLE 13

0.4 g (0.012 moles) of methanol were added to 1.7 g (0.021 moles) of BFME with stirring and cooling 10 ml (0.5 moles). HF or 98% H$_2$SO$_4$ were added and the mixture stirred at room temperature prior to analysis by gas chromatography and mass spectrometry.

| Found: | % (by GC) |
|---|---|
| Bis-fluoromethyl ether (BFME) | 55.0 |
| Fluoro methyl ether | 27.3 |
| Methanol | 7.05 |
| Bis(fluoromethoxy)methane | 0.62 |
| Dimethoxy methane | 8.0 |
| Trioxane | 1.64 |

EXAMPLE 14

Trioxane (10 g,0.33 moles) was added to HF (48 g,2.4 moles) with stirring. Ethanol (1.72 g, 0.037 moles) was carefully added dropwise, with stirring and cooling.

Analysis of the products by mass spectrometry showed the main components to be BFME and the acetal diethoxymethane. Fluoromethyl ethyl ether, C$_2$H$_5$OCH$_2$F, was also identified.

EXAMPLE 15

2-fluoroethanol (4.67 g, 0.073 moles) was added to a mixture of trioxane (5 g, 0.167 moles) in HF (24 g, 1.2 moles). After stirring for 30 minutes, the products were analysed:

| Found | % (by GC) |
| --- | --- |
| BFME | 32.1 |
| Fluoromethyl methyl ether | 1.4 |
| 2-fluoroethanol | 58.5 |
| Fluoromethyl 2-fluoroethyl ether | 6.3 |
| Bis(fluoromethoxy)methane | 0.06 |
| Trioxane | 1.0 |

EXAMPLE 16

1.5 g (0.018 moles) 2,2-difluoroethanol was added to 1.7 g (0.021 moles) BFME. 0.25 ml (0.0125 moles) HF or 98% $H_2SO_4$ were added and the mixture stirred for 20–30 minutes before sampling

| Found: | % (by GC) |
| --- | --- |
| BFME | 31.8 |
| Fluoromethyl 2,2-difluoroethyl ether | 27.3 |
| 2,2 difluoroethanol | 1.6 |
| Bis(fluoromethoxy)methane | 3.1 |
| $CHF_2CH_2OCH_2OCH_2F$ | 3.9 |
| Trioxane | 1.2 |

EXAMPLE 17

3.7 g (0.037 moles) of 2,2,2-trifluoroethanol were added to 3.4 g (0.021 moles) BFME with cooling and stirring. 0.3 ml (0.015 moles) HF or 98% $H_2SO_4$ were added and the mixture sampled after stirring at room temperature for 20–30 minutes.

| Found: | % (by GC) |
| --- | --- |
| BFME | 15.9 |
| Fluoro methyl 2,2,2-trifluoroethyl ether | 63.4 |
| Trifluoroethanol | 1.5 |
| $CF_3CH_2OCH_2OCH_2F$ | 5.8 |
| $CF_3CH_2OCH_2OCH_2OCH_2F$ | 12.3 |

EXAMPLE 18

10 g of 1H 1H 3H-tetrafluoropropanol were added to a mixture of 6 g trioxane in 20 g HF. After stirring the mixture was analysed.

| Found: | % (by GC) |
| --- | --- |
| BFME | 23.6 |
| Fluoromethyl 2,2,3,3 tetrafluoropropyl-ether | 67.0 |
| 1H, 1H, 3H-tetrafluoropropanol | 4.3 |
| Bis(fluoromethoxy)methane | 1.3 |
| $CF_2HCF_2CH_2OCH_2OCH_2F$ | 2.15 |
| Trioxane | 1.5 |

EXAMPLE 19

Trioxane (1 g, 0.033 moles) was added to HF (5 g, 0.25 moles) and the mixture cooled. Hexafluoroisopropanol (2.38 g, 0.0142 moles) was added and the products analysed after 5 minutes stirring.

| Found: | % (by GC) |
| --- | --- |
| BFME | 22.2 |
| $(CF_3)_2CHOCH_2F$ | 4.9 |
| Hexafluoroisopropanol | 71.6 |
| $(CF_3)_2CHOCH_2OCH_2F$ | 1.3 |

EXAMPLE 20

$SbCl_5$ (1.1 g, 0.0051 moles) was added to a cooled vessel containing BFME (2.0 g, 0.0244 moles) and stirred.

The contents of the head above the solution were analysed after 1 hour.

The experiment was then repeated, with the addition of 2 g HF.

| | % (by GC) | |
| --- | --- | --- |
| Found: | without HF | with |
| HF | | |
| BFME | 44.6 | 29.8 |
| Difluoromethane | 19.8 | 18.1 |
| Methyl chloride | 1.7 | 2.8 |
| Chlorofluoromethane | 12.4 | 17.0 |
| Dichloromethane | 3.2 | 8.0 |
| Chloromethyl fluromethyl-ether | 17.6 | 22.4 |
| Bis(chloromethyl)ether | 0.5 | 1.65 |

EXAMPLE 21

$NbCl_5$ (0.3 g, 0.0016 moles) was added to BFME (1.7 g, 0.021 moles) and the head space analysed after stirring for about an hour.

| Found: | % (by infra red) |
| --- | --- |
| BFME | 88.6 |
| Difluoromethane | 0.034 |
| Methyl fluoride | 0.012 |
| Fluoromethyl methyl ether | 0.57 |
| Chloromethyl fluromethyl-ether | 10.5 |
| Bis(chloromethyl)ether | 0.28 |

EXAMPLE 22

Aluminium chloride (0.5 g, 0.06 moles) was added to BFME (2.0 g, 0.0244 moles) with stirring. The head space was analysed by infra red spectroscopy. The experiment was then repeated with the further addition of HF (0.2 g, 0.01 moles).

| | % (by infra red) | |
| --- | --- | --- |
| Found: | without HF | with HF |
| BFME | 97.57 | 87.0 |
| Difluoromethane | 0.044 | 0.17 |
| Methyl fluoride | — | 0.014 |
| Fluoro methyl ether | 0.024 | 0.056 |
| Dichloromethane | — | 0.09 |
| Bis(fluoromethoxy)methane | 0.17 | 0.1 |
| Chloromethyl fluromethyl-ether | 2.19 | 12.56 |

EXAMPLE 23

10 g of paraformaldehyde were added to 48 g HF and the mixture stirred. 15 g of sodium bromide were added, 5 g at a time. On addition of the final 5 g. the mixture separated into two layers. The bottom layer was analysed and found to contain a mixture of BFME, bromomethyl fluoromethyl ether and bis(bromomethyl) ether.

The experiment was repeated using BFME and HBr. HBr was bubbled through BFME (4 g, 0.049 moles) for 5–10 minutes. One layer was observed; this was analysed by mass spectroscopy and found to contain BFME and bromomethyl fluoromethyl ether as the main products, with a small amount of bis(bromomethoxy)methane also present.

EXAMPLES 24–27

In these examples ethers were sparged directly from trioxane/HF equilibrium mixture+alcohol and as such were co-fed with BFME. Reaction products therefore contain $CH_2F_2$ and $CH_3F$ from this source.

EXAMPLE 24

The following composition was sparged over a Hastelloy C (20 ml) catalyst held in a 1" tube at 257° C.

|  | Percentage |
|---|---|
| $CH_3OH$ | 1.61 |
| BFME | 66.8 |
| $CH_3OCH_2F$ | 14.4 |
| Dimethoxymethane | 13.7 |
| Trioxane | 3.4 |

The off gases were scrubbed with water prior to analysis by GC.

| Found | % (by GC) |
|---|---|
| $CH_3F$ | 19.2 |
| $CH_2F_2$ | 60.8 |
| BFME | 20.0 |

EXAMPLE 25

The following composition was sparged over stainless steel rings (115 l) at 324° C.:

|  | % |
|---|---|
| BFME | 14.5 |
| 2,2 difluoroethanol | 42.3 |
| Fluoromethyl 2,2-difluoroethyl ether | 41.4 |

| Found | % (by GC) |
|---|---|
| $CH_2F_2$ | 4.4 |
| $CH_2FCHF_2$ | 23.5 |
| BFME | 44.05 |
| Fluoromethyl methyl-ether | 1.9 |
| 2,2 difluoroethanol | 4.1 |
| Fluoromethyl 2,2,-difluoroethyl ether | 20.9 |

EXAMPLE 26

The following composition was sparged over chromia catalyst (200 ml) at 350° C.:

|  | % |
|---|---|
| $CF_3CH_2OCH_2F$ | 61.3 |
| BFME | 16.8 |
| Trifluoroethanol | 11.0 |
| $CF_3CH_2OCH_2OCH_2F$ | 9.4 |
| Trioxane | 1.6 |

| Found | % (by GC) |
|---|---|
| $CH_3F$ | 31.5 |
| $CH_2F_2$ | 46.6 |
| BFME | 1.0 |
| $CH_3CF_3$ | 0.4 |
| $CF_3CH_2F$ | 13.9 |
| Others | 6.6 |

EXAMPLE 27

The ether/BFME was separated from equilibrium mixture and $CF_2HCF_2CH_2OH$ and the following composition sparged over Hastelloy C (120 ml) at 259° C.

|  | % (by infra red) |
|---|---|
| BFME | 4.1 |
| Fluoromethyl 2,2,3,3-tetrapropyl ether | 68.5 |
| Bis(fluoromethoxy)-ether | 2.1 |
| 1H, 1H, 3H tetra-fluoropropanol | 4.3 |
| $CF_2HCF_2CH_2OCH_2OCH_2F$ | 20.8 |

| Found | % (by infra red) |
|---|---|
| Fluoromethyl 2,2,3,3-tetrafluoropropyl-ether | 60.3 |
| 1H, 1H, 3H tetra-fluoropropanol | 1.0 |
| $CH_3F$ | 1.2 |
| $CH_2F_2$ | 0.7 |
| $CH_2FCF_2CH_2F$ | 12.8 |
| Others | 24.0 |

EXAMPLE 28

Fluoral hydrate (0.5 g, 0.0043 moles) was added to a mixture of paraformaldehyde (1.25 g, 0.0417 moles) and HF (6.0 g, 0.3 moles) and the mixture analysed after stirring for 30 minutes.

| Found | % (by mass spec) |
|---|---|
| BFME | 59.5 |
| Fluoral hydrate | 0.37 |
| $CF_3CHFOCH_2F$ | 27.8 |
| $CF_3CHFOCH_2CH_3$ | 0.29 |
| $CH_2FOCH_2OCH_2F$ | 1.5 |
| Trioxane | 1.79 |

EXAMPLE 29

Methanol (0.6 g, 0.0187 moles) was added to fluoral hydrate (1.7 g, 0.0146 moles) with stirring and cooling. HF (2.2 g, 0.11 moles) was added and the reaction product analysed after stirring.

| Found | % (by infra red) |
|---|---|
| Methanol | 3.6 |
| Fluoral hydrate | 46.4 |
| Methyl 1,2,2,2-tetrafluoroethyl-ether | 48.3 |
| Ethyl 1,2,2,2-tetrafluoroethyl ether | 1.7 |

EXAMPLE 30

Ethanol (1.9 g, 0.041 moles) was added to fluoral hydrate (2.6 g, 0.022 moles) with stirring and cooling. HF (2.0 g, 0.1 moles) was then added and the mixture analysed after 30 minutes stirring.

| Found | % (by infra red) |
|---|---|
| Ethanol | 94.9 |
| Fluoral hydrate | 1.6 |
| Ethyl 1,2,2,2-tetrafluoroethyl-ether | 3.65 |

EXAMPLE 31

2-fluoroethanol (3.0 g, 0.047 moles) was added to fluoral hydrate (4.3 g, 0.037) with stirring and cooling. HF (5.0 g, 0.25 moles) was added and the mixture was analysed after stirring for 30 minutes.

| Found | % (infra red) |
|---|---|
| Fluoral hydrate | 65.1 |
| Methanol | 3.5 |
| Acetaldehyde | 2.8 |
| Trifluoroethanol | 0.8 |
| 2-fluoroethanol | 27.2 |
| 2'-fluoroethyl-1,2,2,2 tetrafluoro-ethyl ether | 0.62 |

EXAMPLE 32

Preparation of Fluoromethyl-2,2,2-trifluoroethyl Ether 100 g of anhydrous HF were added to 20 g of trioxane in a plastic bottle cooled in crushed ice. To the solution was added 50 g of trifluoroethanol. The resulting solution was added slowly to 500 ccs of crushed ice to produce an aqueous and an organic layer. The organic layer was separated off and distilled to give 99% pure ether (G.C/MS., NMR).

Preparation of Catalyst for Decomposition of Ether

The catalysts were sieved to give particles in the range 1.18 mm to 0.25 mm and then packed into a stainless steel tube. They were prefluorinated by sparging HF with nitrogen at a flow rate of 50 ccs per min and passing the vapours over the catalyst at 350° C. for 4 hours.

Decomposition of Ether 5 g of ether were dissolved in 15 g of HF and sparged over the catalyst with nitrogen at a flow rate of 20 cc per min. The off gas was scrubbed with water and analysed by G.C.

| Catalyst | | |
|---|---|---|
| AlF3 @ 400° C. 10cc | unchanged ether | 4.7% |
| | 134a | 49% |
| | 143a | 6.7% |
| | 32 | 22.5% |
| | 41 | 9.2% |
| | CO | 5.1% |
| LaF3 @ 500° C. 1cc | unchanged ether | 75.7% |
| | 134a | 1.8% |
| | 143a | 5.5% |
| | 32 | 11.4% |
| | 41 | 1.9% |
| | CO | 3.0% |
| 90% Fe 203 10% Cr 203 @ 500° C. 10cc | unchanged ether | 16.3% |
| | 134a | 43% |
| | 143a | 4.7% |
| | 32 | 7.7% |
| | 41 | 9.3% |
| | CO | 16.4% |
| 42% CuO 58% Cr 203 @ 400° C. 10cc | unchanged ether | <1% |
| | 134a | 52% |
| | 143a | 26% |
| | 32 | 8% |
| | 41 | 3% |
| | CO | 7% |

EXAMPLE 33

Preparation of Fluoromethyl-1,2,2,2-tetrafluoroethyl Ether, $CF_3CHFOCH_2F$

Trioxane (10 g, 0.33 moles) was added to anhydrous HF (150 g, 7.5 moles) with stirring and cooling. Fluoral hydrate (10 g, 0.086 moles) was added to the mixture which was analysed after 24 hours.

| Found (% by mass spectrometry) | |
|---|---|
| BFME | 46.6 |
| $CF_3CHFOCH_2F$ | 41.05 |
| $CF_3CHFOCH_2OCH_2$ | 5.8 |
| Unknown | 5.2 |
| $CF_3CHFOCH_3$ | 1.3 |

EXAMPLE 34

Ethanol (3.24 g, 0.0704 moles) was added to a cooled, stirred mixture of trioxane (5 g, 0.166 moles) in HF (24 g, 2.2 moles). The products were analysed by GC and mass spectrometry.

| Found (% by mass spec.) | |
|---|---|
| BFME | 36.5 |
| Diethoxy ethane | 35.2 |
| Fluoromethyl ether ether | 17.8 |
| Ethanol | 5.7 |
| BFMM | 2.8 |
| Trioxane | 2.06 |

EXAMPLE 35

Hexafluoroisopropanol (2.38 g, 0.0142 moles) was added to a cooled, stirred mixture of trioxane (1 g, 0.0133 moles) in HF (5 g, 0.25 moles). After stirring for 5 minutes, the mixture was analysed by mass spectrometry.

| | |
|---|---|
| Hexafluoroisoprapanol | 71.6 |
| BFME | 22.2 |
| $(CF_3)_2CHOCH_2F$ | 4.9 |
| $(CF_3)_2choch_2och_2f$ | 1.3 |

We claim:

1. A process for the production of a hydrofluorocarbon which comprises reacting a non-enolisable aldehyde with hydrogen fluoride to form a fluorinated intermediate and reacting the fluorinated intermediate with an alcohol or a fluorinating agent to form an α-fluoroether selected from the group consisting of a fluoromethyl ether and a 1,2,2,2-tetrafluoroethyl ether and heating said α-fluoroether in the vapor phase to convert the α-fluoroether to said hydrofluorocarbon, the α-fluoroether being treated to reduce its water content before its conversion to said hydrofluorocarbon.

2. A process for the production of an α-fluoroether selected from the group consisting of a fluoromethyl ether and a 1,2,2,2-tetrafluoroethyl ether which comprises reacting a non-enolisable aldehyde with hydrogen fluoride to form an equilibrium mixture containing a fluorinated intermediate and adding an alcohol or fluorinating agent to the equilibrium mixture to form said α-fluoroether.

3. A process for the production of an α-fluoroether selected from the group consisting of a fluoromethyl ether and a 1,2,2,2-tetrafluoroethyl ether which comprises reacting a non-enolisable aldehyde with hydrogen fluoride to form a fluorinated intermediate, isolating said intermediate and subsequently reacting said isolated intermediate with an alcohol or fluorinating agent.

4. A process as claimed in claim 1, 2 or 3 wherein a primary alcohol is employed.

5. A process as claimed in claim 1, 2 or 3 wherein the non-enolisable aldehyde is formaldehyde or trifluoroacetaldehyde.

6. The process of claims 1, 2 or 3 wherein the α-fluoroether is heated in the substantial absence of water.

* * * * *